United States Patent [19]
Froix

[11] 3,975,289
[45] Aug. 17, 1976

[54] CHARGE TRANSFER COMPLEXES OF FERROCENES HAVING LIGHT FILTERING PROPERTIES
[75] Inventor: Michael F. Froix, Webster, N.Y.
[73] Assignee: Xerox Corporation, Stamford, Conn.
[22] Filed: Feb. 25, 1974
[21] Appl. No.: 445,388

[52] U.S. Cl. .................. 252/300; 260/439 CY
[51] Int. Cl.² ................................. G02B 5/20
[58] Field of Search .............. 260/439 CY; 252/300

[56] References Cited
OTHER PUBLICATIONS
Brandon et al., "The Reactions of Metallocenes with Electron Acceptors", *J. Org. Chem.* vol. 31, pp. 1214–1217, (Apr. 1966).

Pittman, Jr., "Preparation of Organometallic Polymers of Transition Metals–Potential Applications", *J. Paint Technol* 1971 43 (561), p. 29.

*Primary Examiner*—Benjamin R. Padgett
*Assistant Examiner*—Deborah L. Kyle
*Attorney, Agent, or Firm*—John E. Crowe; James J. Ralabate; James P. O'Sullivan

[57] ABSTRACT

Ferrocene ionic charge complexes of benzoquinones having utility as optical filters capable of absorbing electromagnetic radiations within the range of 3500–6000 Angstrom. The active material can be utilized in a suitable optical system as a liquid filter in the form of a solution, emulsion, gel, etc., or as a film together with suitable light permeable backing or support members.

10 Claims, No Drawings

CHARGE TRANSFER COMPLEXES OF FERROCENES HAVING LIGHT FILTERING PROPERTIES

BACKGROUND OF THE INVENTION

This invention relates to a family of ferrocene ionic charge complexes having utility as filtering materials suitable for use as a filtering component in an optical filter.

Optical filters are well known and widely used devices for passing radiation of selected wavelengths and simultaneously rejecting undesirable wavelengths. One of the most commonly used types of optical filters in the photographic and xerographic mode is the band-pass filter. Generally speaking, such filters comprise alternating layers of a dielectric material having a relatively high index of refraction and a dielectric material having a relatively low index of refraction. By making the layers of the proper thickness, the reflections of certain bands of wavelengths from the boundary between the materials are reenforced and thereby removed from the transmitted beam. The remaining wavelengths, which are grouped together in a plurality of orders having widely spaced bands, pass through the material. Such interference filters generally tend to be expensive because of the problems inherent in their manufacture. Expense notwithstanding, however, the rapid development both in photographic, electrophotographic, and xerographic technology in the area of multicolored records has accented the basic need for new and better filtering means in order to achieve the proper color balance and sensitivity at a price acceptable in the market place.

Generally, a complex formed between an electron donor and an electron acceptor retains the absorptions of the components modified to some extent, together with one or more absorption bands characteristic of the complex as a whole. The extra absorptions characteristic of the complex is readily observed in the interaction is between a strong donor and a strong acceptor. In such cases, the transition appears as a separate band at considerably longer wavelengths than the absorptions of the component molecules. The intensity of the absorption band of a complex is usually determined as the molar extinction coefficient at the wavelength of maximum absorption. However, a direct determination of intensity cannot always be made, due to the high degree of dissociation of the complex in solution.

It is an object of the present invention to obtain a new class of ionic charge transfer complexes which can be readily produced and which can be incorporated into existing photographic and xerographic systems for use as light filtering material.

It is a still further object of the present invention to obtain suitable filtering material which is stable under normal photographic and xerographic conditions and which will efficiently and precisely absorb light within the 3500–6000 Angstrom range.

SUMMARY OF THE INVENTION

The foregoing and other objects and advantages are obtained by the discovery and utilization of a new class of ionic or covalent complexes conveniently represented by the general formula:

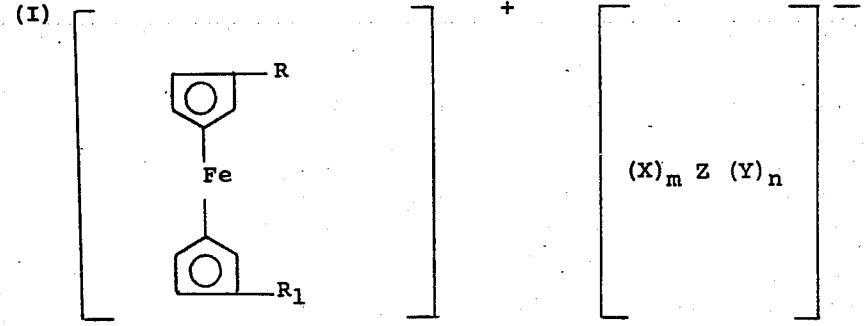

wherein
R, of the electron donor component, is defined as a hydrogen; an alkyl group such as methyl or octyl; an aryl group such as a phenyl or a naphthyl group; an acyl group such as

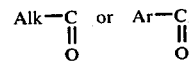

wherein Alk is lower alkyl and Ar is a phenyl or a naphthyl group; a halo group such as chloro or bromo; a halomercuri group such as chloromercuri; an hydroxy lower alkyl group such as hydroxymethyl or hydroxy ethyl or hydroxyoctyl; or a vinyl group of the formula

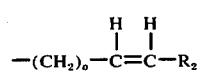

wherein $o$ is defined as 0–4 and $R_2$ is defined as a hydrogen, a halo group such as chloro or bromo; or a lower alkyl group such as methyl;

$R_1$ is separately and independently defined as in R;

Z is defined as an organic electron acceptor which, in combination with any substituent group, is capable of forming a ferrocene complex. Such groups are exemplified, for instance, as a benzoquinonyl group, a benzoquinonylene group, a benzopyranyl group, and a benzofuranyl group, Z being further defined within the above context as an alkylene group of 1–15 carbon atoms such as ethylene or similar groups, or as a phenyl group;

X is defined as a halo group such as chloro, bromo, fluoro; or a nitro group;

Y is defined as a cyano group;

$m$ is defined as an integer of 0–3; and $n$ is defined as an integer of 0–4, the sum of $n$ and $m$ being not less than 2 or greater than 4.

Suitable compounds within the scope of the present invention are readily obtainable, for instance, in accordance with the following general formulae:

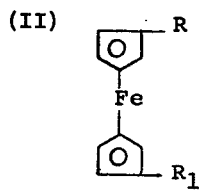   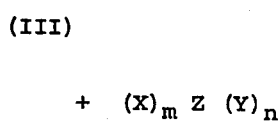

wherein the various substituents, groups and subnumbers are defined as above.

The ion acceptor (Formula III) and the ion donor (Formula II) as described above, are conveniently separately dissolved into suitable organic solvents such as acetonitrile, benzene or methylene chloride, and the solutions slowly admixed in approximate molar amounts at a reaction temperature varying from about −10°C. to 25°C. and preferably at about 0°C.–20°C. The resulting complex is readily separated out as a precipitate by evaporation under vacuum and filtration, and the product washed with acetonitrile or similar organic solvents in which the product is relatively insoluble.

The metal-containing ion donor reactant (Formula II) is obtainable, for instance, by a Grignard synthesis, using a suitable organic Grignard and Ferric Chloride as described on pages 906–7 of "Advanced Organic Chemistry" by Fieser, 5th ed., Reinhold Publishing Corporation. Such material is obtainable commercially from "Research Organic/Inorganic Chemical Corporation" of Sun Valley, California.

Suitable reactants for producing filtering complexes in accordance with the above-described invention are further exemplified in TABLE I with respect to suitable reactants within Formula I and tetracyanoethylene in equimolar amounts using acetonitrile as a solvent.

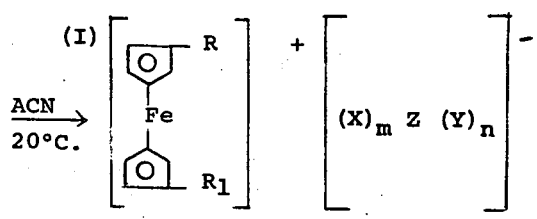

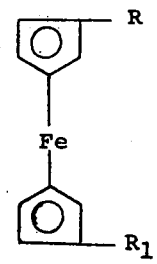

TABLE I

| Complex | R | $R_1$ | $E_{ct}(1)$* | $E_{ct}(2)$* |
|---|---|---|---|---|
| 1 | $CH_3CO-$ | $CH_3CO-$ | 16,100 | 13,900 |
| 2 | $\overset{O}{\underset{\|}{CH}}-$ | H | 13,700 | 12,400 |
| 3 | $CH_3-\overset{O}{\underset{\|}{C}}-$ | H | 12,500 | 10,900 |
| 4 | Cl-Hg- | H | 10,900 | 9,650 |
| 5 | $OH-CH_2$ | H | 11,200 | 10,350 |
| 6 | Cl-Hg- | Cl-Hg- | 11,100 | 9,650 |
| 7 | H | H | 10,520 | 9,302 |
| 8 | $CH_2=CH-$ | H | 12,200 | 8,650 |
| 9 | $CH_3-$ | $CH_3$ | 9,500 | 8,200 |
| 10 | $CH_3-$ | H | 10,300 | 8,900 |

*Charge transfer maxima of ferrocenes - TCNE complexes in methylene chloride.

Additional reactants suitable for producing light filtering complexes in accordance with the present invention are set forth in TABLE II, below, with reference to Formulae II and III reacted in equimolar amounts at 20°C. in acetonitrile.

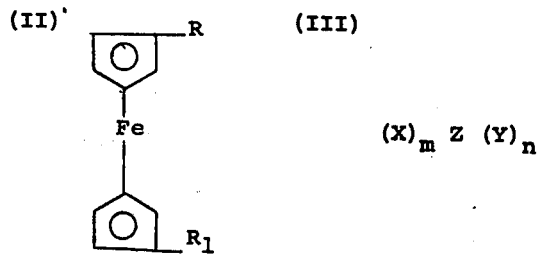

TABLE II

| Complex | R | $R_1$ | Z | X | Y | m | n |
|---|---|---|---|---|---|---|---|
| 11 | H | H | benzoquinonyl | Cl | CN | 2 | 2 |
| 12 | $HC{=}C-$ H H | H | " | Cl | CN | 2 | 2 |
| 13 | H | H | " | Br | — | 4 | — |
| 14 | Cl-Hg- | Cl-Hg- | " | Br | — | 4 | — |
| 15 | H | H | " | Cl | — | 4 | — |
| 16 | $OH-C_4H_9-$ | $OH-C_4H_9-$ | " | Cl | — | 4 | — |
| 17 | H | H | " | F | — | 4 | — |
| 18 | $CH_2=CH-$ | H | " | F | — | 4 | — |
| 19 | H | H | quinodimethane | — | CN | — | 4 |
| 20 | $CH_3CO-$ | $CH_3CO-$ | " | — | CN | — | 4 |
| 21 | H | H | phenyl | $NO_2$ | — | 3 | — |
| 22 | $C_4H_8=CH-$ | H | " | $NO_2$ | — | 3 | — |

Since variations in selective blocking occur depending upon the atomic structure of the particular complexes produced, it is oftentimes convenient to utilize a composit filter made up of a plurality of filtering elements. For testing or certain research purposes, however, it is often convenient to utilize a filter consisting of a standard spectrophotometric cell containing about 2% by weight of complex in a solvent such as methylene chloride.

Another possibility involves dispersion of washed and dried solid complex in gelatin, sandwiched between glass plates or by surface dyeing. The latter (i.e. imbibition) usefully employs a polycarbonate or cellulose acetate medium with a 10% solution of one or more complexes described above for about 1 hour.

In an imbibition process, several solvents can be used as a carrier liquid for transporting a disperse-type dye (i.e. complex) into the support medium. Care must be exercised in the use of dye carriers which have a solvent action on the support, however, because any degredation in surface quality will adversely affect the optical clarity of the resulting filter.

Many additional useful modifications and techniques for utilizing organic optical filtering materials are described or referred to in Kirk Othmer — "Encyclopedia of Chemical Technology", Vol. 9, 2nd ed., pages 244–263.

The invention will be further illustrated by reference to the following specific examples:

EXAMPLE I (Complex 12)

About 50 ml of a 0.01 mole solution of vinylferrocene (obtained commercially) in acetonitrile is admixed with a corresponding amount of a 0.01 molar solution of 2,3-dichloro-5,6-dicyanobenzoquinone at about 20°C. After about 1 minute, the reaction mixture turns a deep burgundy color. The resulting product is thoroughly admixed, diluted to 1/10 concentration and tested for light absorption properties on a Beckman spectrophotometer. A comparable solution of vinyl ferrocene in acetonitrile is used as a control. The absorption spectra is reported in TABLE III below.

TABLE III

| Vinylferrocene/Acetonitrile | | Vinylferrocene-DDQ/Acetonitrile | |
|---|---|---|---|
| τ | Reading | τ | Reading |
| 3100 | .80 | 3100 | .80 |
| 3500 | .35 | 3500 | .45 |
| 3800 | .08 | 3800 | .28 |
| 4000 | .14 | 4000 | .28 |
| 4200 | .27 | 4200 | .28 |
| 4700 | .27 | 4700 | .28 |
| 5000 | .15 | 5000 | .28 |
| 5500 | .01 | 5500 | .28 |
| 6000 | .01 | 6000 | .28 |
| 6100 | 0 | 6100 | .20 |
| 6200 | 0 | 6200 | .10 |
| 6300 | 0 | 6300 | .04 |
| 6500 | 0 | 6500 | .01 |

EXAMPLE II

The reaction material of Example I is partly evaporated under vacuum, filtered and the dye complex washed three times in benzene and dried under vacuum. One gram of the resulting product is pulverized, thoroughly admixed with an equal weight of gelatin and cast on optical glass at an average thickness of about 100 μ. The resulting absorption spectrum substantially agrees with the results reported in Example I, demonstrating an sharp drop in absorption at about 3500 and 6000 Angstrom.

EXAMPLE III (Complex 3)

0.01 Mole of tetracyanoethylene is slowly reacted with acetyl ferrocene in acetonitrile at about 20°C. in the manner of Example I to obtain a reaction product which is filtered, washed with benzene and identified as Complex 3. Charge transfer maxima of the resulting complex dissolved in methylene chloride are reported in TABLE I.

Other modifications of the present invention will become apparent to those skilled in the art upon reading the above disclosure. These modifications also fall within the scope of the present invention.

What is claimed is:

1. An optical filter comprising a filtering element containing a complex represented by the formula:

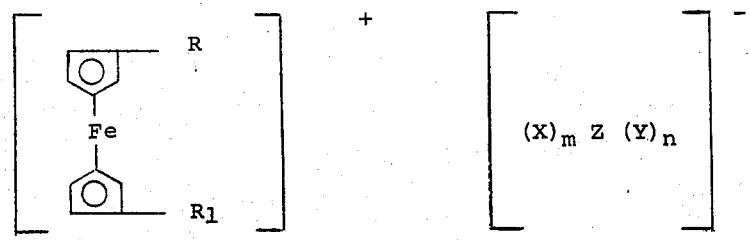

wherein R is defined as, an aryl group, an acyl group, a halo group, a halomercuri group, a hydroxy-lower alkyl group, or a vinyl group of the formula:

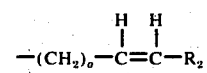

wherein $o$ is defined as 0–4 and $R_2$ is defined as a hydrogen, a halo group or a lower alkyl group;

$R_1$ is separately and independently defined as hydrogen, alkyl or as in R;

Z is defined as an organic electron acceptor which, in combination with any substituent groups, is capable of forming a ferrocene complex;

X is defined as a halo or a nitro group;

Y is defined as a cyano group;

$m$ is defined as an integer of 0–4; and $n$ is defined as an integer of 0–4, the sum of $m$ and $n$ being not less than 2 or greater than 4.

2. An optical filter of claim 1 wherein Z is defined as a benzoquinonyl group.

3. An optical filter of claim 1 wherein Z is defined as an alkylene group.

4. An optical filter of claim 1 wherein Z is defined as an aryl group.

5. An optical filter of claim 2 wherein X is a bromo, fluoro or nitro group; Y is a cyano group; *m* is 0–4; and *n* is 0–4.

6. An optical filter of claim 3 wherein Z is an alkylene group of 1–8 carbon atoms; Y is a cyano group; *m* is 0; and *n* is 4.

7. An optical filter of claim 4 wherein Z is a phenyl group; X is a nitro group; *m* is 3; and *n* is 0.

8. An optical filter of claim 5 wherein R is a vinyl group, a halomercuri group, a halo group, or a hydroxy lower alkyl group; and $R_1$ is separately and independently defined as hydrogen or R.

9. An optical filter comprising a filtering element containing a complex represented by the formula:

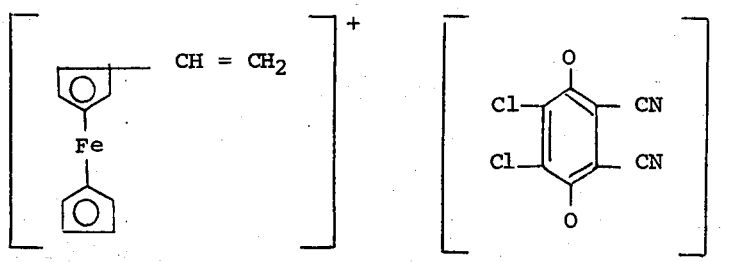

10. An optical filter comprising a filtering element containing a complex represented by the formula:

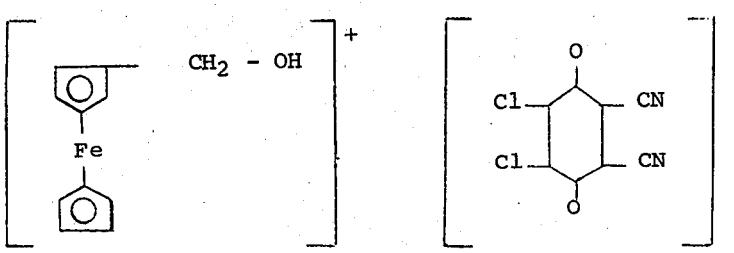

* * * * *